(12) United States Patent
Bell et al.

(10) Patent No.: US 6,186,969 B1
(45) Date of Patent: Feb. 13, 2001

(54) WRIST BRACE

(75) Inventors: Jessica Ann Bell, Mason; Richard Taylor, Cincinnati, both of OH (US); Ralph Michael Buschbacher, Carmel, IN (US)

(73) Assignee: Beiersdorf Inc., Wilton, CT (US)

( * ) Notice: Under 35 U.S.C. 154(b), the term of this patent shall be extended for 0 days.

(21) Appl. No.: 09/365,626

(22) Filed: Aug. 2, 1999

(51) Int. Cl.[7] ................................................. A61F 13/00
(52) U.S. Cl. ............................................................. 602/64
(58) Field of Search ................................. 602/5, 20, 21, 602/22, 60, 61, 62, 63, 64; 128/877, 878, 879; 2/16, 18, 19, 159, 161.1, 161.2, 161.4, 161.6, 161.7; D2/361; 473/59, 61, 62, 63

(56) References Cited

U.S. PATENT DOCUMENTS

| | | |
|---|---|---|
| D. 259,955 | 7/1981 | Helferich ............................... D24/64 |
| D. 306,364 | 2/1990 | Hamilton ............................... D29/20 |
| D. 339,866 | 9/1993 | Rice ..................................... D24/190 |
| D. 340,990 | 11/1993 | Kawamura ............................ D24/190 |
| D. 357,745 | 4/1995 | Radwell ................................ D24/190 |
| 3,710,790 * | 1/1973 | Lemon .................................... 602/21 |
| 4,309,991 * | 1/1982 | DeMarco ............................. 602/64 X |
| 4,584,993 | 4/1986 | Nelson ................................... 128/77 |
| 4,854,309 | 8/1989 | Elsey ..................................... 128/87 |
| 5,014,689 | 5/1991 | Meunchen et al. . |
| 5,421,811 | 6/1995 | Moore et al. .......................... 602/21 |
| 5,513,657 | 5/1996 | Nelson ................................. 128/879 |
| 5,725,490 * | 3/1998 | Conran ................................... 602/21 |
| 5,728,059 | 3/1998 | Wiesemann et al. ................. 602/64 |
| 5,769,166 | 6/1998 | Nelson et al. ......................... 602/21 |
| 5,769,804 | 6/1998 | Harris et al. .......................... 602/21 |
| 5,769,808 * | 6/1998 | Mattijs ................................... 602/64 |
| 6,013,044 * | 1/2000 | Estwanik .............................. 602/64 |
| 6,024,715 * | 2/2000 | Maxwell ............................... 602/64 |

* cited by examiner

*Primary Examiner*—Kim M. Lee
(74) *Attorney, Agent, or Firm*—Norris, Mclaughlin & Marcus, P.A.

(57) ABSTRACT

Wrist brace comprising a sheet of flexible material having a first portion which is substantially non-stretchable and a second portion which is stretchable, said first and second portions being joined along a junction extending from the distal edge of said sheet to the proximal edge of said sheet.

9 Claims, 5 Drawing Sheets

WRIST BRACE

BACKGROUND OF THE INVENTION

This invention relates to orthopedic wrist braces, more particularly, to a novel wrist brace which combines elastic and nonelastic fabric in its construction. The novel wrist brace makes it possible to vary the compression on the proximal portion of the wrist which is sought to be immobilized, while at the same time retaining freedom of movement of the distal portion of the hand.

A wide variety of wrist support devices are known in the art. These include various types of sleeves and wraps, some of which are adjustable and some of which are not.

A recent improvement in the state of the art is disclosed in U.S. Pat. No. 5,728,059, which discloses a wrist support comprised of a sheet of flexible elastic material having pockets for a rigid splint. The splint is formed with a curvature to conform to the user's wrist and palm. With the splint inserted into one of the pockets, the wrist support is wrapped around the wrist and hand and secured in place with a plurality of fastening wraps. The compression applied to the wrist by the wrist brace is adjustable by the fastening wraps, the position of which effects the degree of stretch of the elastic fabric, and thereby the compression on the wrist and hand.

U.S. Pat. No. 5,769,804 describes a wrist brace which comprises a preformed shell, with an elastic tongue which extends across the shell (after the manner of a tongue in a shoe). The patient's hand is inserted into and through the shell, after which the shell is tightened using a multi-string lace extending over the elastic tongue. The device is said to provide even distribution of all forces to immobilize the wrist, but, having a shell composed of a three-layer composite including a thermoformable plastic, would appear to be relatively inflexible. In addition, the need to apply tension to the laces at the same time the fastening straps to which said laces are attached are latched makes this device relatively complicated to use.

The prior art devices generally apply uniform compression over and around all portions of the wrist and hand to which they are applied. It would, however, be desirable to be able to apply greater compression to the proximal wrist, where it is needed, while at the same time maintaining a lesser compression on those portions of the hand where such compression is not needed and increased flexibility is desired.

It is therefore an object of the present invention to provide a wrist brace which enables the amount of compression applied to the regions of the hand and wrist to be different, so that a higher compression can be applied to the proximal wrist area while a lesser compression is applied to the distal hand region.

It is a further object of the invention to provide a wrist brace which is easily applied and adjusted.

It is yet a further object of the present invention to provide a wrist brace which combines the convenience of an elastic slip-on sleeve, with the adjustable tensioning advantages of an open-wrap brace.

It is still a further object of the present invention to provide an elastic wrist brace which avoids the use of natural latex.

SUMMARY OF THE INVENTION

These and other objects are achieved by the wrist brace of the present invention, which comprises a sheet of flexible material having a distal edge, proximal edge and opposite lateral edges; a first of said lateral edges being substantially straight and a second lateral edge being provided with a plurality of fastening straps extending laterally, and being fastenable to an outer surface of said sheet of flexible material, a first portion of said sheet being formed of an inelastic material and a second portion of which is formed of an elastic material, said first and second portions being joined along a generally spiraled junction extending from the distal edge of said sheet to the proximal edge of said sheet, said junction being closer to said first lateral edge at the distal edge and spaced further apart from said first lateral edge at the proximal edge of said sheet, the inside surface of said sheet comprising a sleeve of elastic material attached to the inelastic portion of said sheet, generally along said first lateral edge, said sleeve opening to accommodate the thumb of a patient to whom the wrist brace is to be applied.

The elastic material from which the sleeve is formed may be the same or different than the elastic material forming the elastic portion of the sheet of flexible material.

In a preferred embodiment, the wrist brace of the present invention further comprises a pocket, running longitudinally between the proximal edge and the distal edge, secured on the outside surface of the sheet opposite the sleeve, such as by sewing, and having an inward kink at the distal end thereof. The pocket is adapted to accommodate a substantially inflexible splint, which itself is adapted to the anatomy of the inner surface of the hand. The splint may be made of, for example, aluminum or plastic.

It is also preferred that the fastening straps and the outside surface of the sheet material be provided with complementary hook and loop fastening means, such as that sold under the trademark VELCRO®, although other fastening means, such as buckles, snap-on connectors and the like could also be used.

In a further preferred embodiment, at least one of the fastening straps is of a length sufficient to wrap completely around the wrist of a patient when the wrist brace is applied to the patient's wrist.

In a particularly preferred embodiment, the wrist brace includes a substantially inflexible splint inserted in the longitudinal pocket, said splint having a curvature at its distal end to fit the concave palmer area above the lunate bone.

Optionally, the splint is reversible to fit either the left hand or the right hand.

These and other aspects, features and advantages of the present invention will become apparent from the following detailed description taken in conjunction with the accompanying drawings.

DETAILED DESCRIPTION

Figure 1:
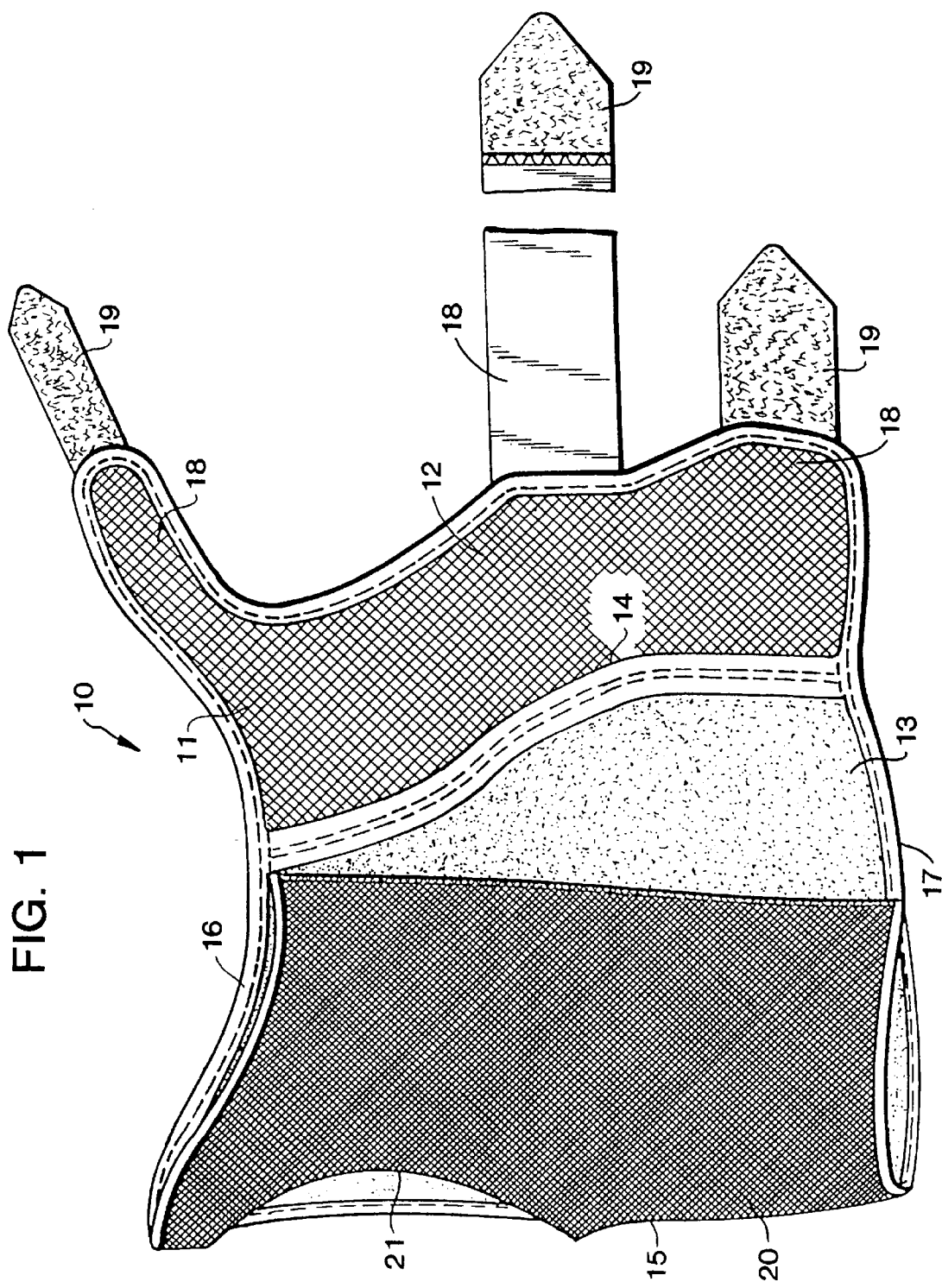
FIG. 1 is a top view of the inside surface of the wrist support of the present invention.

The wrist brace 10, shown in FIG. 1, is formed of a sheet 11 of flexible material having a stretch portion 12 and a non-stretch portion 13 joined to each other along a generally spiraled junction 14. The spiraled junction is closer to lateral edge 15 at distal edge 16 than it is to lateral edge 15 at proximal edge 17. The width of the elastic portion 12 of sheet 11 is thus greater at the distal portion and narrower at the proximal portion of the sheet.

The inside surface of wrist brace 10 is provided with a sleeve 20 of elastic material attached to the inelastic portion 13 of wrist brace 10, generally along lateral edge 15. Since sleeve 20 is mainly intended to hold the wrist brace in position prior to tightening, the elastic material used to construct sleeve 20 can be of the same or different degree of elasticity as that of the elastic portion 12 of sheet 11. The material of which sleeve 20 is constructed can therefore be chosen to provide comfort and ease when inserting the hand into the sleeve, or can be chosen to be tight-fitting for additional support.

Also shown in FIG. 1 are fastening straps 18 having one portion 19 of complementary hook and loop fasteners, said portion being either the hook portion or the loop portion.

Figure 2:
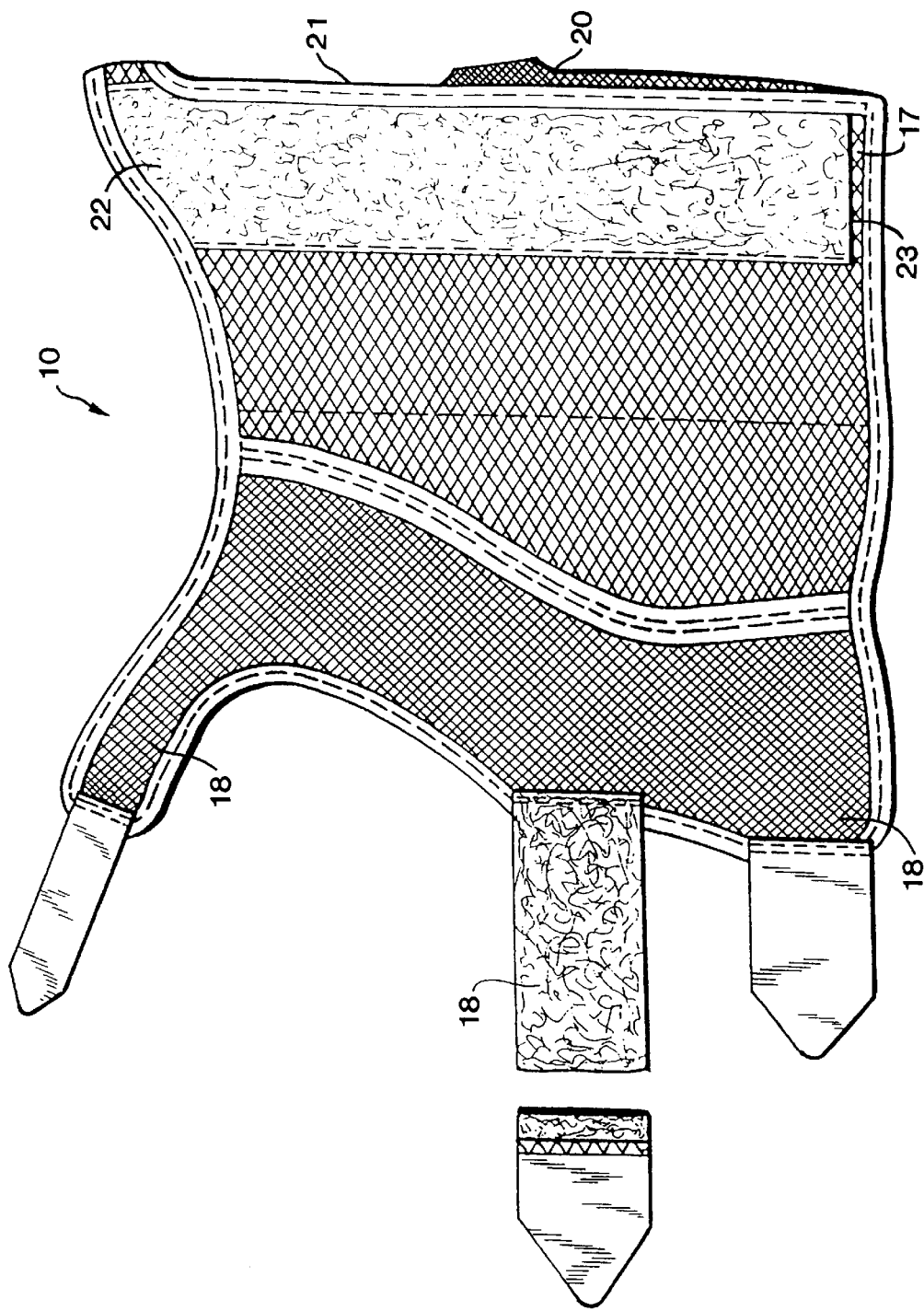
FIG. 2 is a top view of the outside surface of the wrist support of the present invention.
Figures 8, 8A, 9, 9A:
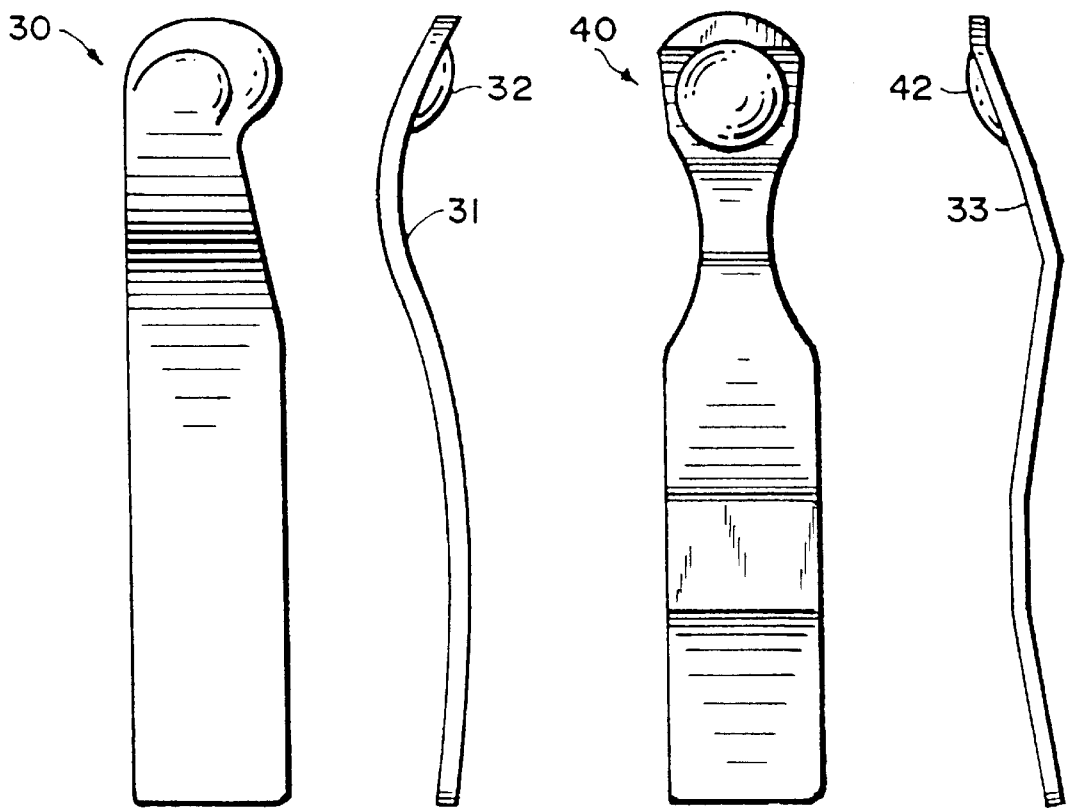
FIG. 8 is a front view of the splint used with the wrist brace.
FIG. 8A is a side view of the splint of FIG. 8.
FIG. 9 is a front view of an alternative splint used with the wrist brace.
FIG. 9A is a side view of the splint of FIG. 9.

FIG. 2 shows the opposite side of the wrist brace shown in FIG. 1. In FIG. 2, sleeve 20 is depicted having a thumb hole 21 and a longitudinal pocket 23 into which a splint, as shown in FIGS. 8 and 9, may be inserted.

The exposed surface of pocket 23 is provided with a portion of hook and loop fastening material 22 that complements the portion of hook and loop material 19, so that 19 is attachable to 23 by said hook and loop means. The hook and loop fastening portion 22 may, alternatively, be located at another position on the outside surface of wrist brace 10 instead of or in addition to the location on the exposed surface of pocket 23.

Figure 3:
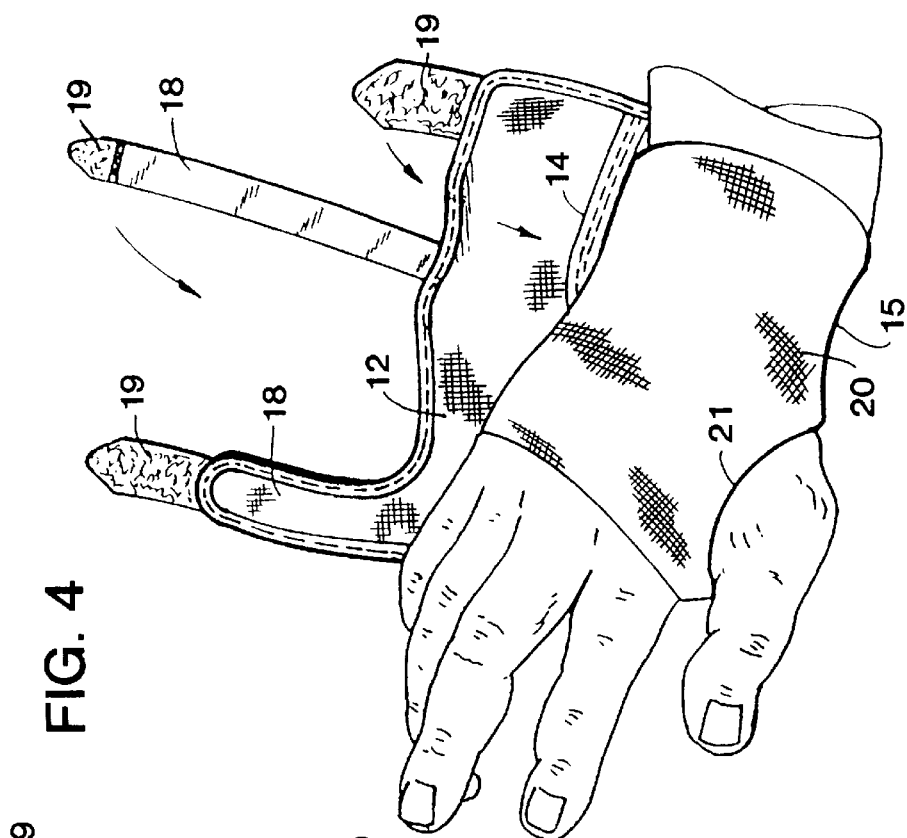
FIG. 3 is a top view of the inside surface of the wrist support, showing the back of a hand which is partially inserted into the sleeve thereof.

FIG. 3 depicts a hand inserted into sleeve 20.

Figure 4:
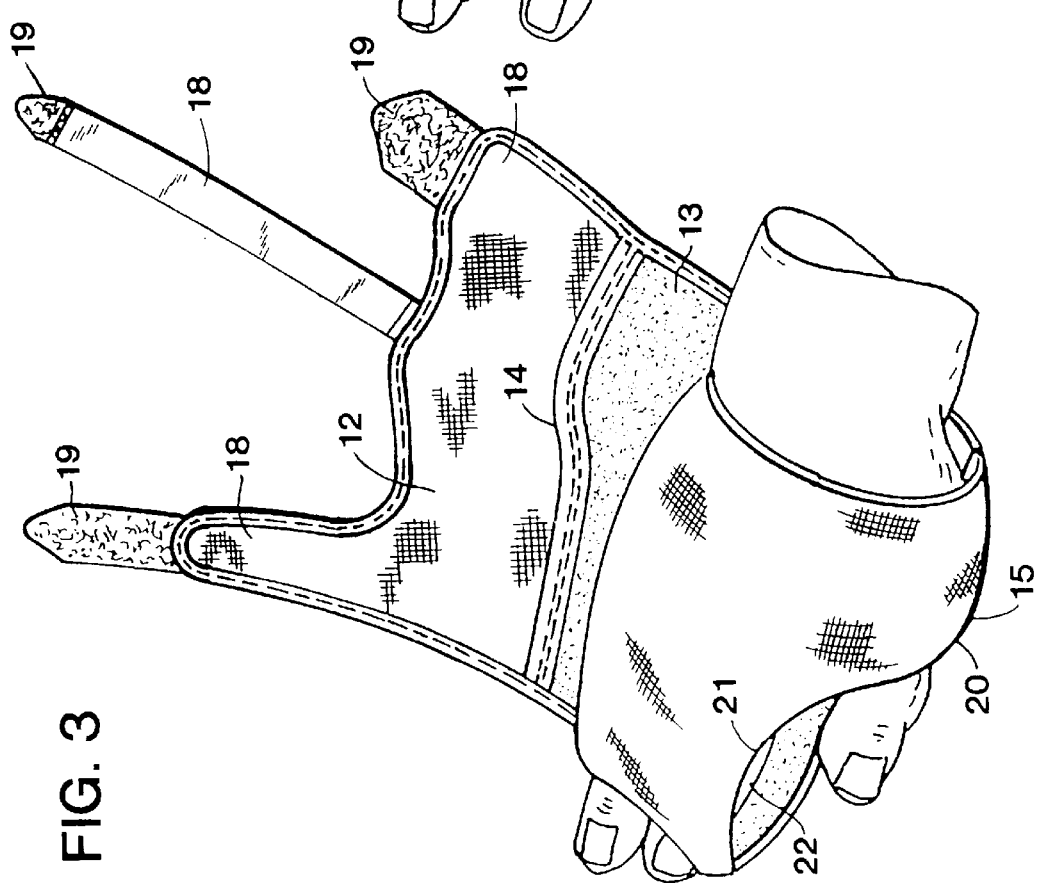
FIG. 4 is a view of the wrist support as shown in FIG. 3, but with the hand fully inserted in the sleeve and the free end of the wrist support being moved towards closure.

FIG. 4 depicts the edge of the wrist brace shown in FIG. 3, with the fastening straps 18 being moved towards sleeve 20.

Figure 5:
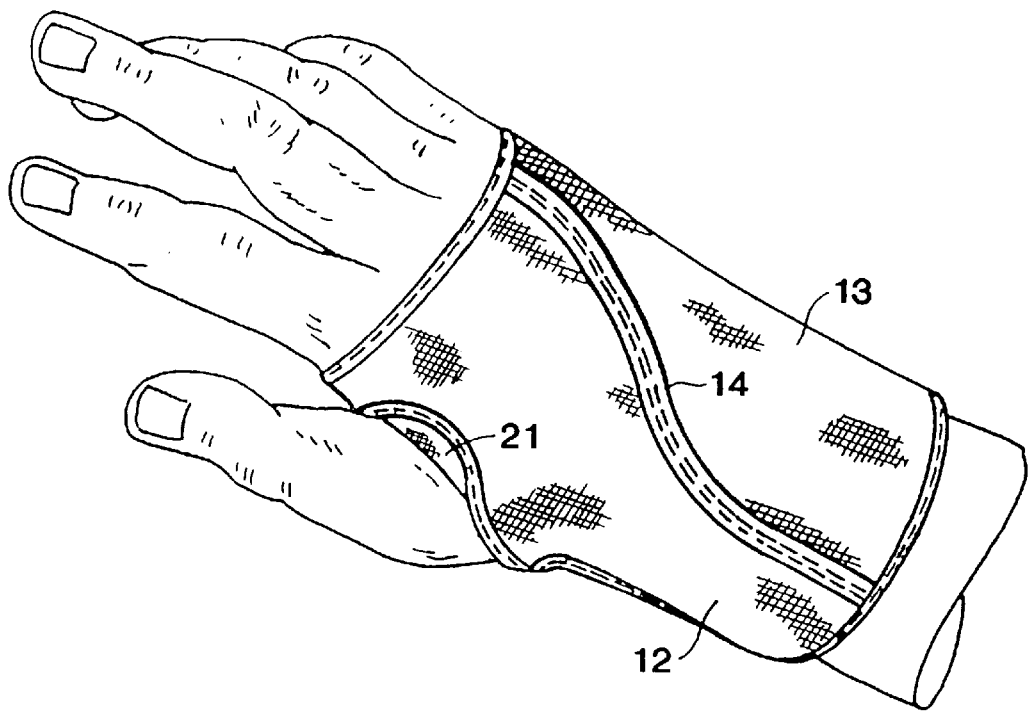
FIG. 5 is a view of the wrist support as shown in FIG. 4, in the fully closed position.

FIG. 5 shows back-hand side of the wrist brace secured by attaching hook and loop portion 19 to the complementary hook and loop portion 22 on pocket 23, while the thumb of the hand passes through thumb hole 21.

Figure 6:
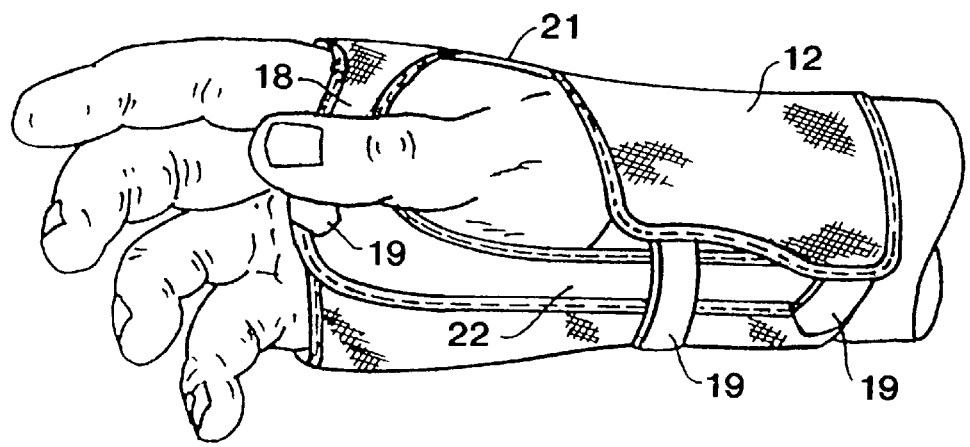
FIG. 6 depicts the wrist support of FIG. 5, viewed from the palmer side.

FIG. 6 shows the attachment of hook and loop portion 19 of straps 18 to complementary hook and loop portion 22.

Figure 7:
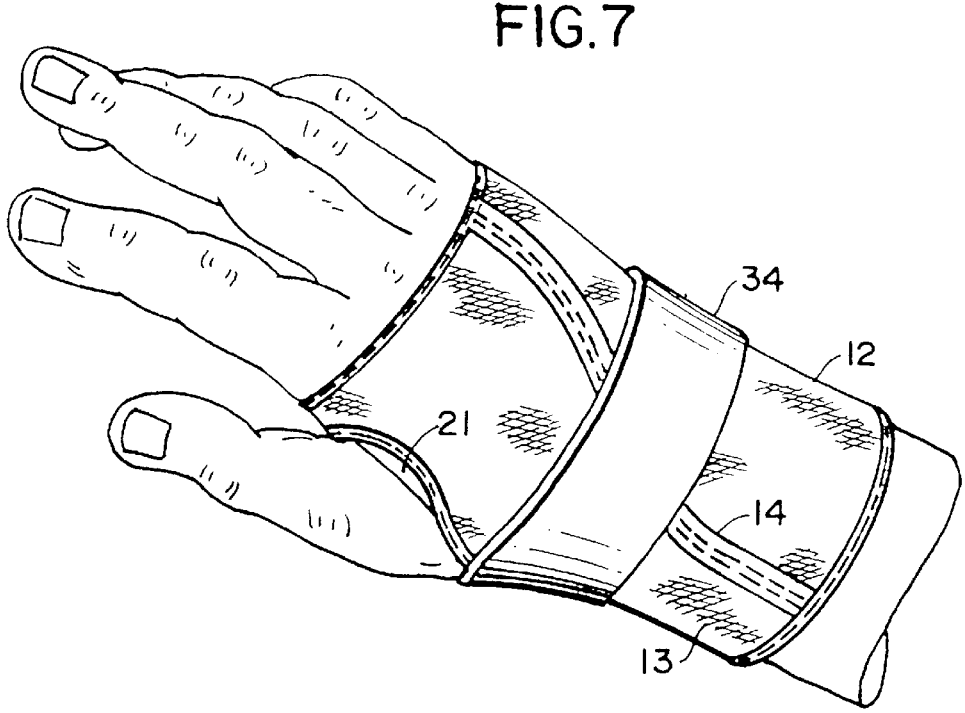
FIG. 7 depicts the wrist brace of the invention, having a strap of sufficient length to be wrapped completely around the wrist of a patient.

In a particularly preferred embodiment, at least one of the fastening straps 18, particularly preferably the middle strap, is constructed of a length sufficient to wrap completely around the wrist, as shown in FIGS. 1 and 7.

FIGS. 8 and 9 illustrate alternative configurations of the splint 30, 40 which can be inserted into pocket 23 of the wrist support. FIGS. 8 and 9 illustrate frontal views of the splints, and FIGS. 8A and 9A illustrate side views.

The splint 30 is an elongated member, preferably of a thin, rigid material such as metal or plastic. The splint material may also be chosen to provide some flexibility to permit limited flexion and extension movement of the user's wrist. The longitudinal and lateral dimensions of the splint are selected so that it fits in the pocket 23 to extend substantially from the proximal end to the distal end of the wrist support 10. The splint 30 is shaped with a curvature 31, as shown in the side view of FIG. 8A, or a bend 33, as shown in FIG. 9A, to conform to the palm and wrist of the user to maintain the hand slightly in extension relative to the wrist.

The splint optionally further includes a convex surface 32, 42 to conform with the palmar cavity of the user's hand.

As shown in FIG. 8, the convex surface 32 may be formed by simply pressing one side of the splint to produce a concave hollow therein, thereby forming a complementary convex surface on the opposite side.

The non-stretch portion 13 of wrist brace 10 may be constructed of any fabric that is non-stretchable or substantially non-stretchable. Preferably, the material will be one that contains no natural latex, since in some cases, natural latex products can cause allergic reactions to skin that is in contact with it. The non-stretch material should also be comfortable to the skin, and breathable, so that moisture can pass through it from the skin to the atmosphere. The material is preferably dimensionally stable. There are a wide variety of materials that will meet these criteria, such as the material marketed by GEHRING TEXTILES, INC.® as SPACER FABRICS, and those marketed by GUILFORD HILLS, INC. as COOL FLEX™ fabric. A further example of fabric that can be used as the non-stretch portion of wrist brace 10 is that disclosed in U.S. Pat. No. 5,385,036.

The stretch portion of wrist brace 10 can be constructed of any of a variety of flexible and elastic materials. Such materials may be of the type that is elastic in one direction only, in which case stretch portion 12 of wrist brace 10 will be elastic in the lateral direction only; or the materials may be elastic in both the lateral and longitudinal directions. The stretch portion of wrist brace 10 preferably contains no natural latex or natural latex products.

Representative materials usable for this purpose are any material possessing elastic properties; for example, woven, non-woven or knit elastics, neoprene, neoprene blends, foams or laminates.

Sleeve 20 is preferably constructed of a fabric, which is stretchable in both lateral and longitudinal directions, and can be the same or different than that of stretch portion 12 of the wrist brace. Particularly preferred materials are any material possessing elastic properties; for example, woven, non-woven or knit elastics, neoprene, neoprene blends, foams or laminates.

The foregoing has described the preferred principles, embodiments and modes of operation of the present invention, however, the invention should not be construed as limited to the particular embodiments discussed. Instead, the above-described embodiments should be regarded as illustrative rather than restrictive, and it should be appreciated that variations, changes and equivalents may be made by others without departing from the scope of the present invention as defined by the following claims.

We claim:

1. A wrist brace comprising a sheet of flexible material having an inner surface, an outer surface, a distal edge, proximal edge and opposite lateral edges; a first of said lateral edges being substantially straight and a second lateral edge being provided with a plurality of fastening straps extending laterally, and being fastenable to the outer surface of said sheet of flexible material, a first portion of said sheet being formed of a substantially non-stretchable material and a second portion of which is formed of a stretchable material, said first and second portions being joined along a junction extending from the distal edge of said sheet to the proximal edge of said sheet, said junction being closer to said first lateral edge at the distal edge and spaced further apart from said first lateral edge at the proximal edge of said sheet, the inner surface of said sheet comprising a sleeve attached to the non-stretchable portion of said sheet, generally along said first lateral edge, said sleeve being provided with an opening to accommodate the thumb of a patient to whom the wrist brace is to be applied.

2. The wrist brace of claim 1, wherein said junction is a generally spiraled junction.

3. The wrist brace of claim 1, wherein said sleeve is constructed of material which is stretchable in both longitudinal and lateral directions.

4. The wrist brace of claim 3, wherein said stretchable material is a woven fabric stretchable in the lateral direction, longitudinal direction, or both directions.

5. The wrist brace of claim 1, further comprising a pocket, extending longitudinally between the proximal edge and the distal edge of said sheet, secured on the outer surface of said sheet opposite said sleeve and adapted to accommodate a substantially inflexible splint.

6. The wrist brace of claim 1, wherein said fastening straps and the outer surface of said sheet are provided with complementary hook and loop fastening means.

7. The wrist brace of claim 1, wherein at least one of said fastening straps is of a length sufficient to wrap completely around the wrist of the patient the wrist brace is applied to the patient's wrist.

8. The wrist brace of claim 5, further comprising a substantially inflexible splint, inserted in said pocket.

9. The wrist brace of claim 8, wherein said splint has a curvature adapted to fit the concave palmar area above the lunate bone, and is reversible to fit either the left hand or the right hand.

* * * * *